United States Patent [19]
Wilson et al.

[11] Patent Number: 5,464,443
[45] Date of Patent: Nov. 7, 1995

[54] PROSTHETIC DEVICE FOR AMPUTEES

[75] Inventors: Greg S. Wilson, Broomfield; John C. Dinsmoor, III, Westminster; Russell C. Miller, Pine, all of Colo.

[73] Assignee: RIK Medical, L.L.C., Boulder, Colo.

[21] Appl. No.: 56,654

[22] Filed: May 3, 1993

[51] Int. Cl.⁶ ...................................................... A61F 2/80
[52] U.S. Cl. ............................................ 623/37; 623/36
[58] Field of Search ................................. 623/37, 36, 33, 623/34, 35

[56]  References Cited

U.S. PATENT DOCUMENTS

| Re. 15,006 | 12/1920 | Lawrence . | |
|---|---|---|---|
| 49,234 | 8/1865 | Coombs | 623/37 |
| 49,529 | 8/1865 | Jewett . | |
| 578,222 | 3/1897 | Donaldson et al. . | |
| 598,452 | 2/1898 | Tullis . | |
| 623,741 | 4/1899 | Riebel . | |
| 708,685 | 9/1902 | White . | |
| 980,457 | 1/1911 | Toles | 623/37 |
| 2,696,011 | 6/1951 | Galdik . | |
| 3,237,319 | 3/1966 | Hanson | 36/2.5 |
| 3,393,407 | 7/1968 | Kandel . | |
| 3,548,420 | 12/1970 | Spence . | |
| 3,663,973 | 5/1972 | Spence . | |
| 3,798,799 | 3/1974 | Hanson et al. | 36/2.5 |
| 3,909,855 | 10/1975 | Barredo . | |
| 4,038,762 | 8/1977 | Swan, Jr. | 36/89 |
| 4,083,127 | 4/1978 | Hanson | 36/93 |
| 4,128,903 | 12/1978 | Marsh et al. . | |
| 4,144,658 | 3/1979 | Swan, Jr. | 36/117 |
| 4,229,546 | 10/1980 | Swan, Jr. | 521/55 |
| 4,243,754 | 1/1981 | Swan, Jr. | 521/55 |
| 4,255,202 | 3/1981 | Swan, Jr. | 102/122 |
| 4,307,056 | 12/1981 | Meyer | 264/222 |
| 4,432,101 | 2/1984 | Johnson . | |
| 4,588,229 | 5/1986 | Jay | 297/459 |
| 4,655,779 | 4/1987 | Janowiak | 623/37 |
| 4,660,238 | 4/1987 | Jay | 5/431 |
| 4,726,624 | 2/1988 | Jay | 297/459 |
| 4,728,551 | 3/1988 | Jay | 428/76 |
| 4,730,610 | 3/1988 | Graebe . | |
| 4,761,843 | 8/1988 | Jay | 5/431 |
| 4,842,330 | 6/1989 | Jay | 297/4 |
| 4,923,474 | 5/1990 | Klasson et al. | 623/33 |
| 4,923,475 | 5/1990 | Gosthnian et al. | 623/37 |
| 4,952,439 | 8/1990 | Hanson | 428/72 |
| 5,018,790 | 5/1991 | Jay | 297/458 |
| 5,058,291 | 10/1991 | Hanson | 36/117 |
| 5,108,456 | 4/1992 | Coonan, III | 623/37 |
| 5,133,776 | 7/1992 | Crowder | 623/37 |
| 5,147,685 | 9/1992 | Hanson | 428/189 |
| 5,156,629 | 10/1992 | Shane et al. | 623/37 |
| 5,201,780 | 4/1993 | Dinsmoor | 5/455 |

FOREIGN PATENT DOCUMENTS

| 2540138 | 3/1977 | Germany | 623/37 |

Primary Examiner—David H. Willse
Attorney, Agent, or Firm—W. Scott Carson

[57]  ABSTRACT

A prosthetic device primarily intended for use by amputees and in particular, leg amputees. The prosthesis includes a relatively rigid, support shell dimensioned to receive a portion of the residual limb and a pad member having a plurality of pouches at least partially filled with fluid. The pad member substantially encircles the leg with its fluid pouches being positioned adjacent one another about and along the leg. Each pouch is supported between the leg and the shell and has inner and outer pouch layers with the fluid being contained between them. Portions of each inner layer fold back on one another to form wrinkles wherein slack is maintained in the inner layer so that it can conform to the user's leg without hammocking or being drawn taut. It can also accommodate and move with the user's leg relative to the support shell without being tensioned or distended.

41 Claims, 9 Drawing Sheets

PROSTHETIC DEVICE FOR AMPUTEES

BACKGROUND OF THE INVENTION

1. Field of the Invention

This invention relates to the field of prosthetic devices for amputees and more particularly, to the field of prosthetic devices for leg amputees.

2. Discussion of the Background

One of the most difficult problems facing amputees is obtaining a prosthesis (e.g., artificial limb) which can be worn comfortably over a long period of time. This is particularly true for leg amputees as the prosthetic device must bear the user's weight yet avoid applying excess pressure to the critical anatomical areas of the residual limb including the distal end, nerves, veins, bones, and tendons. In doing so, the user's weight is preferably distributed over the greatest amount of residual limb area; and, the contact pressure about and along the weight bearing surfaces of the residual limb is preferably uniform.

In addition to weight bearing, the prosthesis must also maintain alignment and stability of the residual limb by providing lateral support about it. Such support is crucial for proper gait of the user; and, it must be provided without unduly creating pressure on the critical anatomical areas. Equally desirable is the minimization and preferably elimination of any movement and rubbing (shear) between the prosthesis and the user's skin as he or she walks or otherwise moves about. Also, the prosthesis would preferably accommodate minor fluctuations in the volume of the residual limb (e.g., swelling and shrinkage due to, among other things, heat, weight gain or loss, and retention of bodily fluids). These fluctuations are common and affect the critical anatomical areas.

Conventional prostheses are able to accommodate many of the above issues; however, all such prior prostheses sacrifice in one or more areas to provide what is felt to be an optimal balance. These sacrifices often result in an improper fit of the prosthesis with accompanying pain, skin damage to the residual limb, and/or inability to maintain proper attachment of the prosthesis. With the above in mind, the present invention was developed in an effort to accommodate all of these issues.

BRIEF DESCRIPTION OF THE DRAWINGS

Fluid 7 is a view similar to FIG. 3 showing the manner in which the inner layers of the fluid pouches can move with the leg.

SUMMARY OF THE INVENTION

This invention is directed to a prosthetic device primarily intended for use by amputees and in particular, leg amputees. The prosthesis includes a relatively rigid, support shell dimensioned to receive a portion of the residual limb. It also includes a pad member having a plurality of pouches at least partially filled with fluid. In the preferred embodiment, the pad member substantially encircles the leg with its fluid pouches being positioned adjacent one another about and along the leg. Each pouch is supported between the leg and the shell and has inner and outer pouch layers with the fluid being contained between them.

The inner layer of each pouch is positioned toward the user's leg and is made of flexible material. Additionally, it is supported so that portions of each inner layer fold back on one another to form wrinkles. In this manner, slack is maintained in the inner layer so that it can conform to the user's leg without hammocking or being drawn taut. It can also accommodate and move with the user's leg relative to the support shell without being tensioned or distended. The adjacent pouches preferably have overlapping and abutting boundary segments with the wrinkling or folding of the inner layers of each pouch preferably occurring predominantly at these boundary segments. In this way, the inner layers of adjacent pouches can move or slide relative to each other to accommodate the user's leg size and shape. They can also move or slide relative to each other to accommodate the user's slight movements relative to the support shell. In doing so, the boundary segments of adjacent pouches preferably remain adjacent and abutting one another to maintain the pressure in adjacent pouches substantially uniform about and along the leg. Additionally, this essentially eliminates any pressure points and maintains full contact with the residual limb.

In the preferred embodiment, the fluid pouches are arranged in two, horizontal rows about the leg for increased lateral stability. A substantially annular pouch is also provided below the bottom row of pouches. The annular pouch encircles the pressure sensitive end of the leg and provides additional support and comfort for it. The preferred embodiment further includes a stretchable backing fabric surrounding the outer layers of the pouches. The stretchable and elastic fabric accommodates slight changes in the leg due to shrinkage and swelling and also helps to firmly hold the fluid pouches in place at all times. Small, supplemental pads containing fluid are also provided which can be selectively placed between the stretchable fabric and the outer layers of the pouches. These pads serve to refine or fine tune the fit of the prosthesis for additional comfort and stability.

DETAILED DESCRIPTION OF THE PREFERRED EMBODIMENTS

Figure 1:
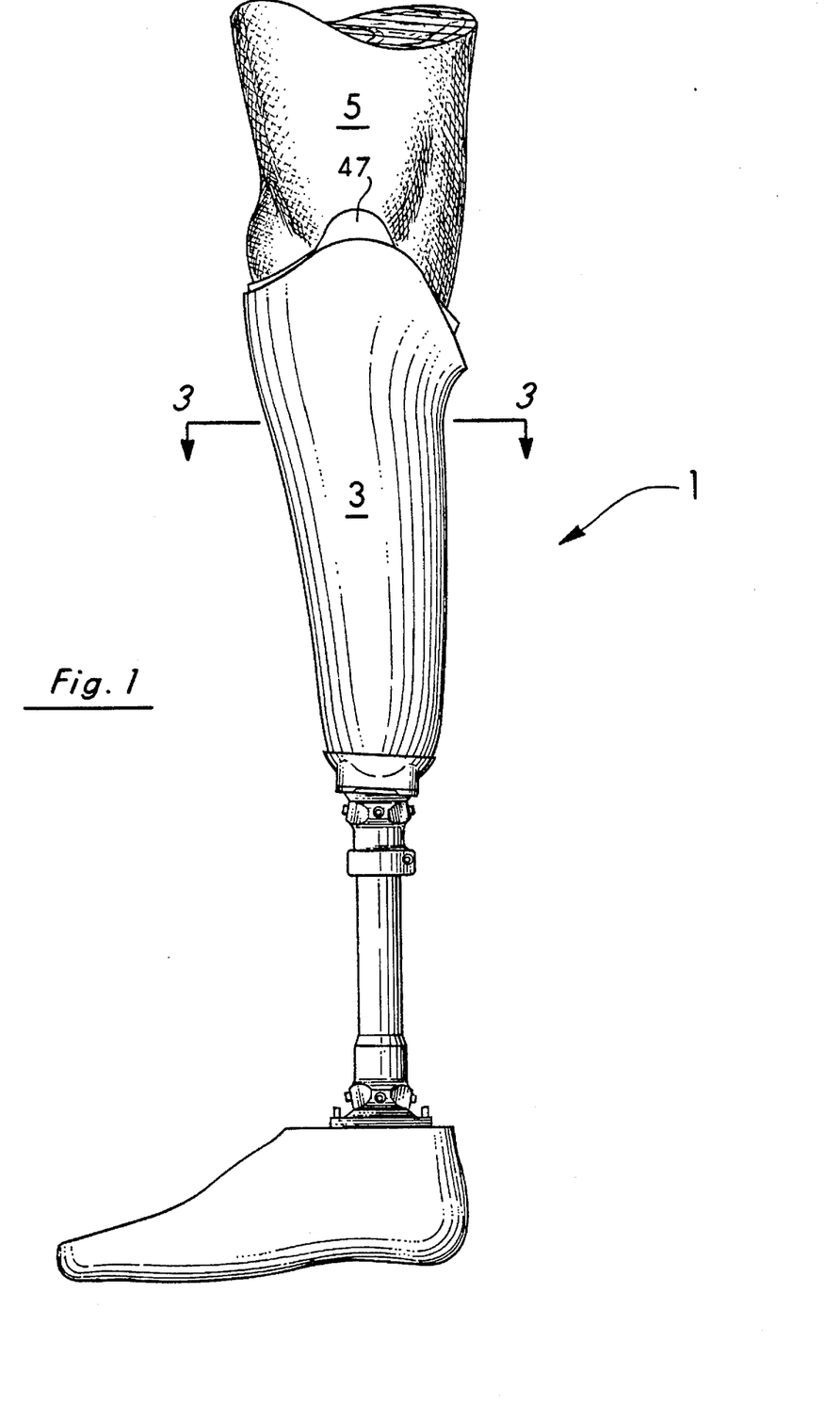
FIG. 1 illustrates the present invention adapted for use in a below the knee prosthesis.
Figure 2:
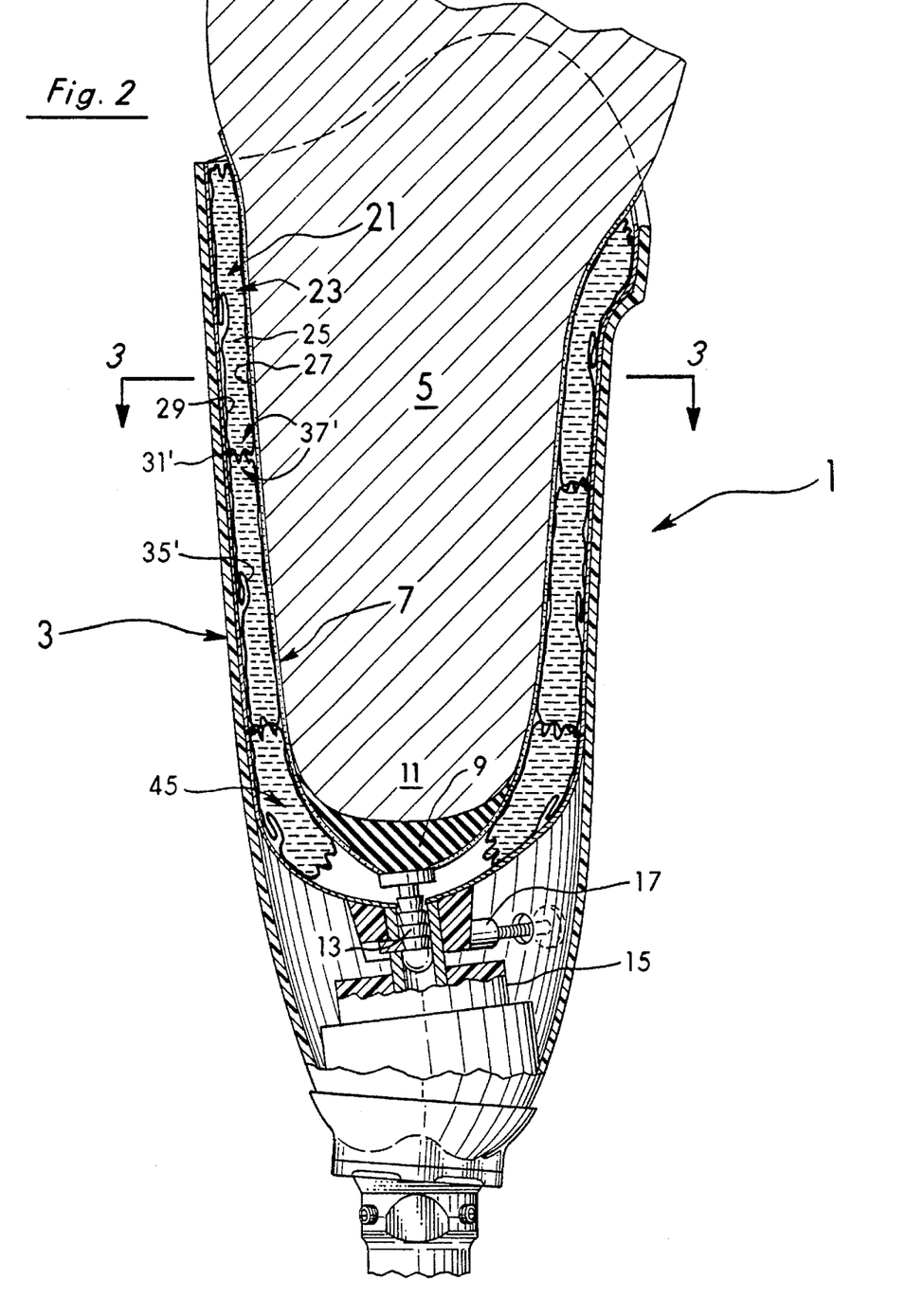
FIG. 2 is a cross-sectional view of the prosthesis in use taken along line 2—2 of FIG. 3.

The prosthetic device 1 of the present invention is shown in FIG. 1 adapted for use in a below the knee prosthesis. As illustrated in FIGS. 1 and 2, the prosthesis 1 includes a relatively rigid, support shell 3 which is dimensioned to receive a portion of the residual limb 5 therein (see FIG. 2). In use, the residual limb 5 typically has a conventional silicone impregnated sock 7 surrounding it with the sock 7 having a padded end portion 9 to protect the pressure sensitive end 11 of the residual limb 5. Attached to the end of the sock 7 is a serrated post 13 which is releasably secured in the socket joint 15 in a conventional manner by the spring-biased dog arrangement 17.

Figure 3:
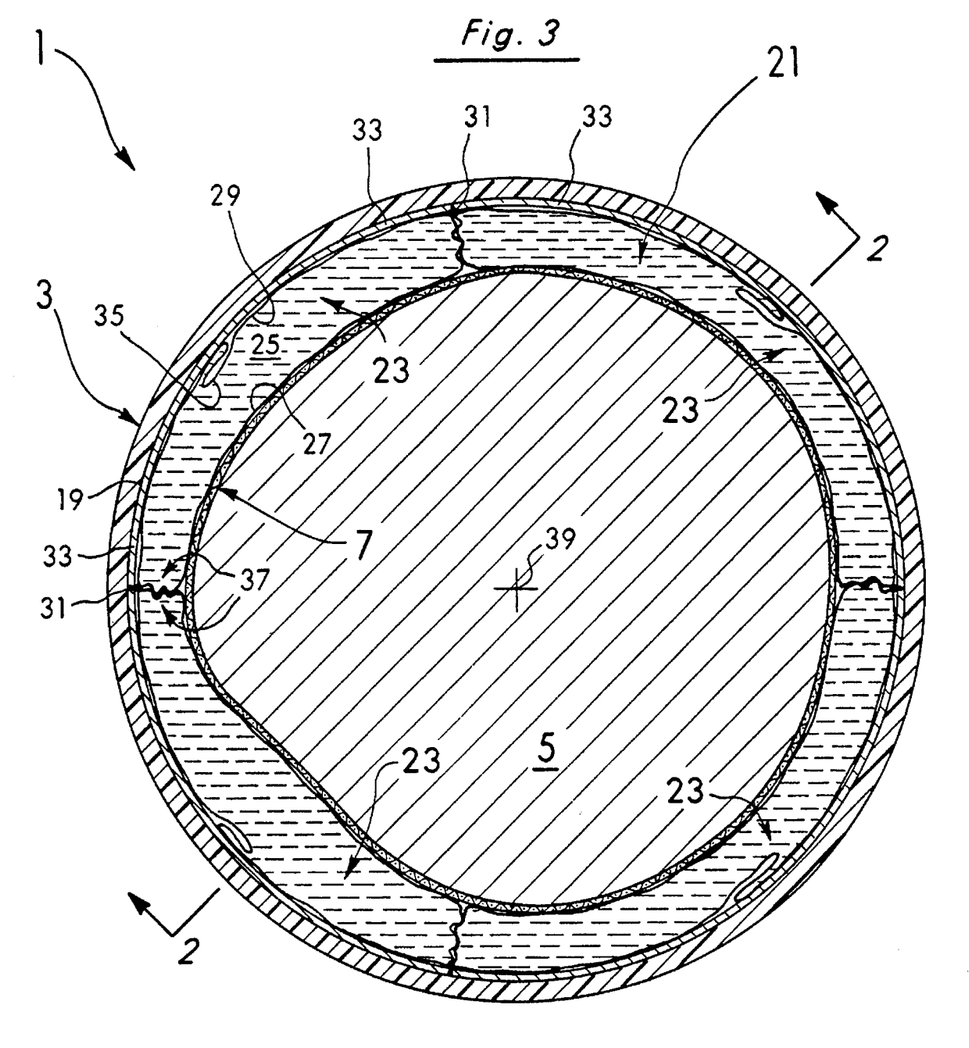
FIG. 3 is a cross-sectional view taken along line 3—3 of FIG. 1.
Figure 4:
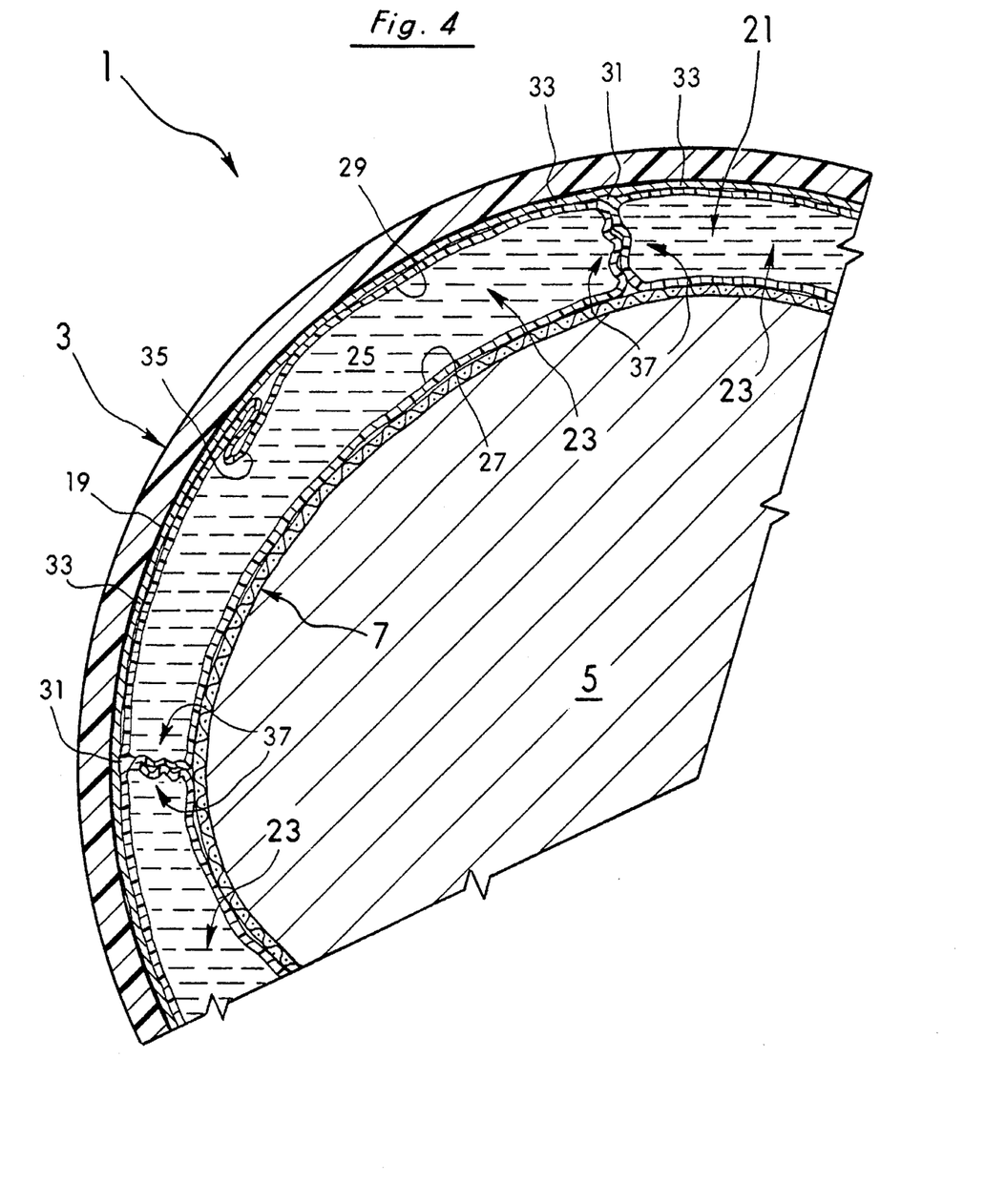
FIG. 4 is an enlarged view of a portion of FIG. 3.
Figure 5:
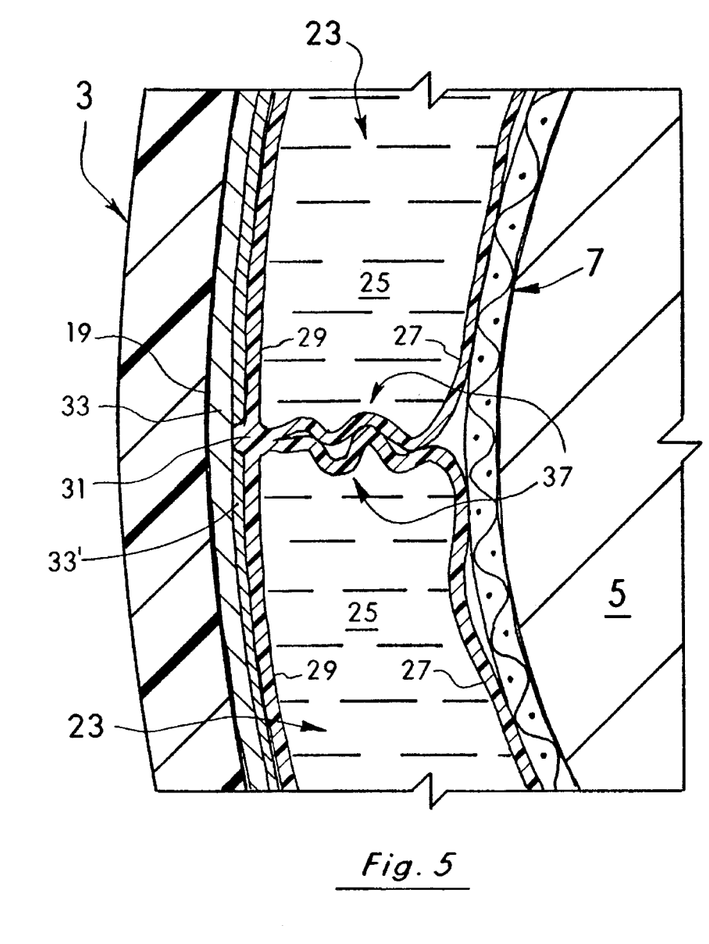
FIGS. 5 and 6 are enlarged views illustrating the relative movement between boundary segments of adjacent fluid pouches in the present invention.

Positioned between the residual leg 5 and the inner surface 19 of the support shell 3 (see FIGS. 3 and 4) is a pad member 21 encircling the residual limb 5. The pad member 21 has a plurality of pouches 23 at least partially filled with fluid 25. As best seen in the enlarged FIG. 4, each pouch 23 has an inner layer 27 toward the leg 5 (which has a sock 7 on it) and an outer layer 29 with the fluid 25 confined therebetween. The peripheral edges of the inner and outer layers 27 and 29 are heat sealed or otherwise joined (e.g., sewn, spot welded) at 31 to each other. The layers 27 and 29 are also joined to the stretchable backing fabric 33 (e.g., Lycra) which preferably has a thin layer 33' of urethane on its inner surface (see FIG. 5). Referring again to FIGS. 3 and 4, the stretchable and elastic backing fabric or layer 33 is dimensioned smaller than the outer layer 29 of the pouch 23 so that the outer layer 29 ends up folding over itself such as at 35 in these FIGS. 3 and 4. The inner layer 27 of each pouch 23 is made of flexible material and is dimensioned as best seen in FIG. 4 to extend in a loose or slack manner between heat seals 31. In this way, wrinkles or folds are created in each layer 27 particularly in the boundary segments 37 where adjacent pouches 23 abut one another (see FIGS. 4 and 5).

Figure 6:
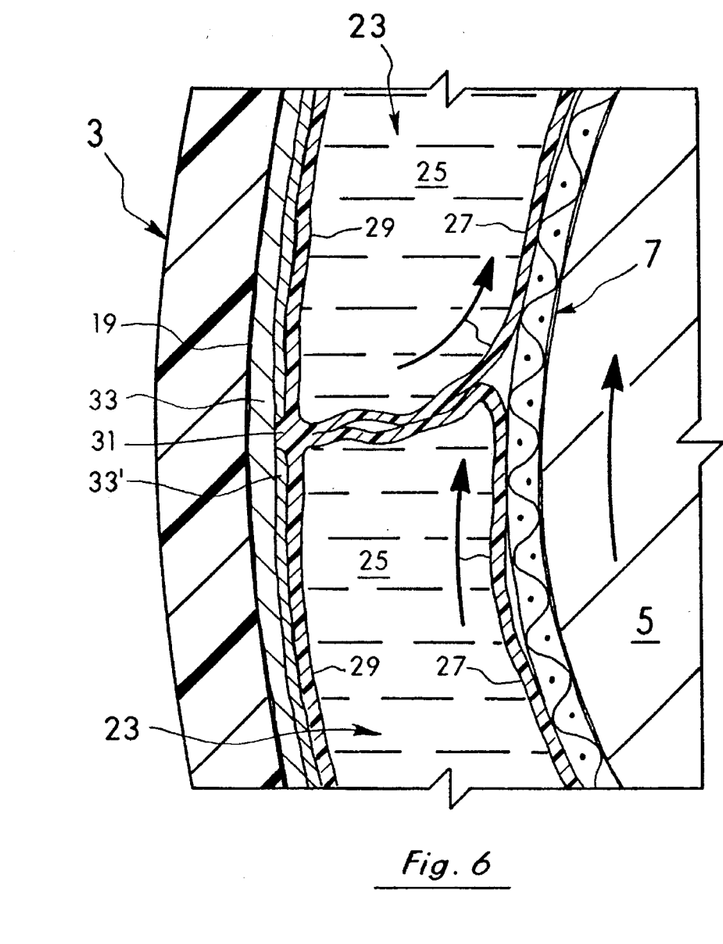
Figure 7:
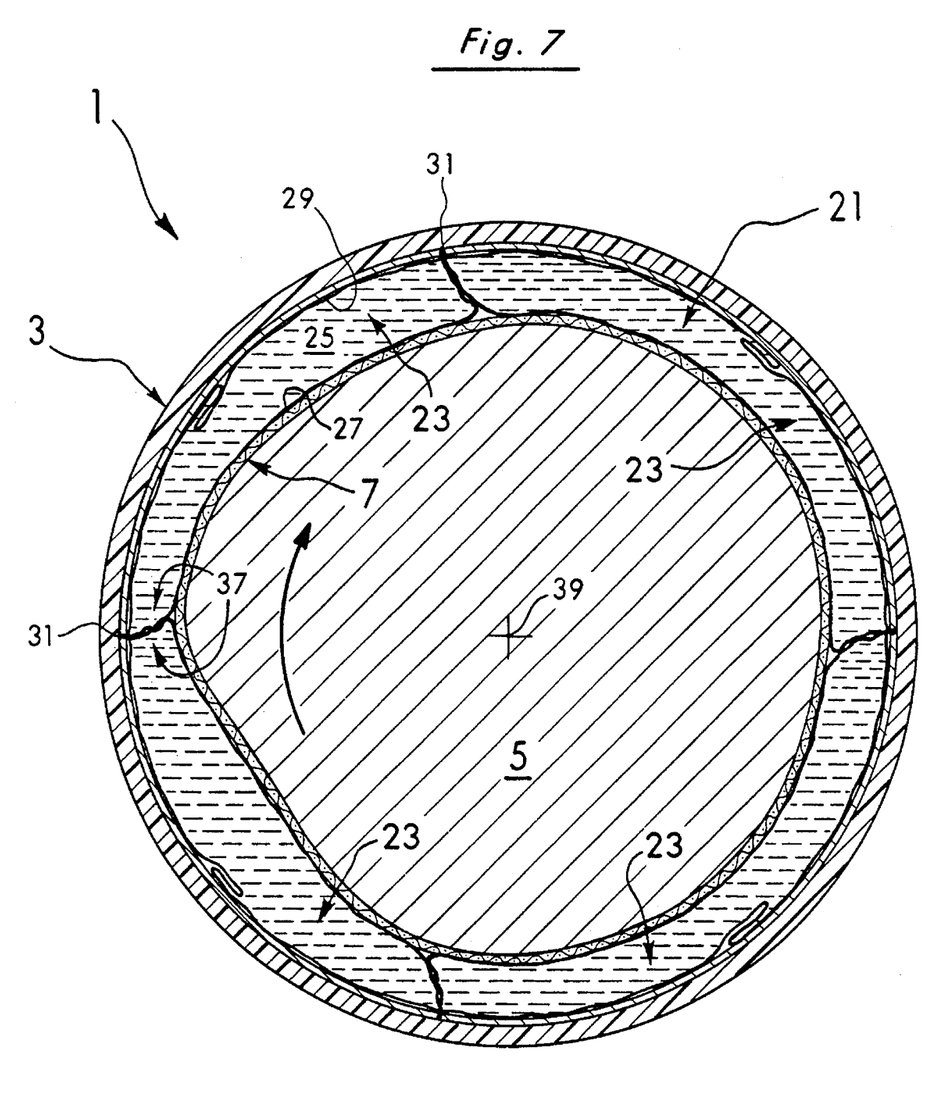

This abutting of boundary segments 37 of adjacent pouches 23 accomplishes two primary functions. First, it substantially equalizes fluid pressure in adjacent pouches 23 to thereby apply a substantially uniform pressure about the residual limb 5 (see FIG. 3). Second, it allows the inner layers 27 of the pouches 23 to move with the leg 5 radially about the axis 39 relative to the support shell 3 (compare FIGS. 3 and 7). In doing so, the inner layers 27 of adjacent pouches 23 can move relative to each other particularly in the boundary segments 37. This movement of adjacent boundary segments 37 is best illustrated in the enlarged views of FIGS. 5 and 6 in which the boundary segments 37 are shown to be supported so that they can actually slide relative to each other as they move with the leg 5. Consequently, there is no rubbing or abrasion between the leg 5 (with the sock 7 on it) and the inner layers 27. Rather, the shearing or displacement takes place within the fluid 25 itself of the pouches 23. The inner layer 27 of each pouch 23 in this regard moves relative to its outer layer 29 which is supported to be substantially fixed in position relative to the support shell 3.

The fluid 25 in the pouches 23 is preferably incompressible with a viscosity of at least one and more preferably is a highly viscous liquid such as disclosed in U.S. Pat. No. 4,588,229. Such preferred liquids exhibit non-resilient, non-restoring properties typical of plastic or viscous thixotropic materials which flow gradually when pressure is applied to them but which maintain their shape and position in the absence of pressure. However, other highly viscous fluids such as gels, oil, or grease can also be used. Additionally, as discussed above, each pouch 23 is preferably only partially filled with fluid so that there is no distending or tensioning of layers 27 in use.

Referring again to FIGS. 4–6, the slack in the inner layer 27 of each pouch 23 allows wrinkles or folds to occur anywhere between the heat seals 31; but, they are preferably concentrated in the boundary segments 37 away from the contact areas between the inner layer 27 and the leg 5 (with the sock 7 on it). With such wrinkling or folding, each inner layer 27 is essentially prevented from being distended or placed under tension between its boundary segments 37 even during movement with the leg 5 radially about the axis 37 relative to the support shell 3 (see FIG. 6). In substantially the same manner and for substantially the same reasons, there is no tensioning or distending of the inner layers 27 with any movement of the leg 5 along the axis 39. This is accomplished as explained in more detail below because the horizontally extending boundary segments 37' (see FIG. 2) are made and operate in essentially the same manner as the vertically extending boundary segments 37 illustrated in FIGS. 3–7.

Figure 8:
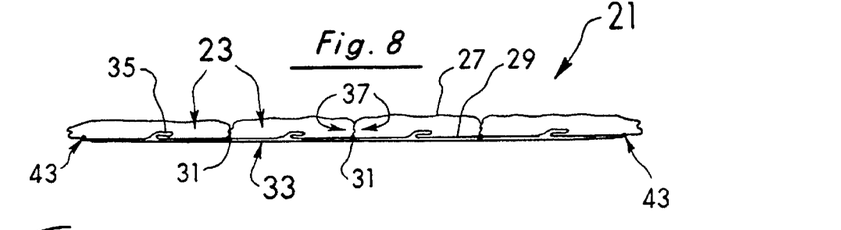
FIG. 8 is a schematic, cross-sectional view of the pad member of the present invention in an unwrapped or laid open position.
Figure 9:
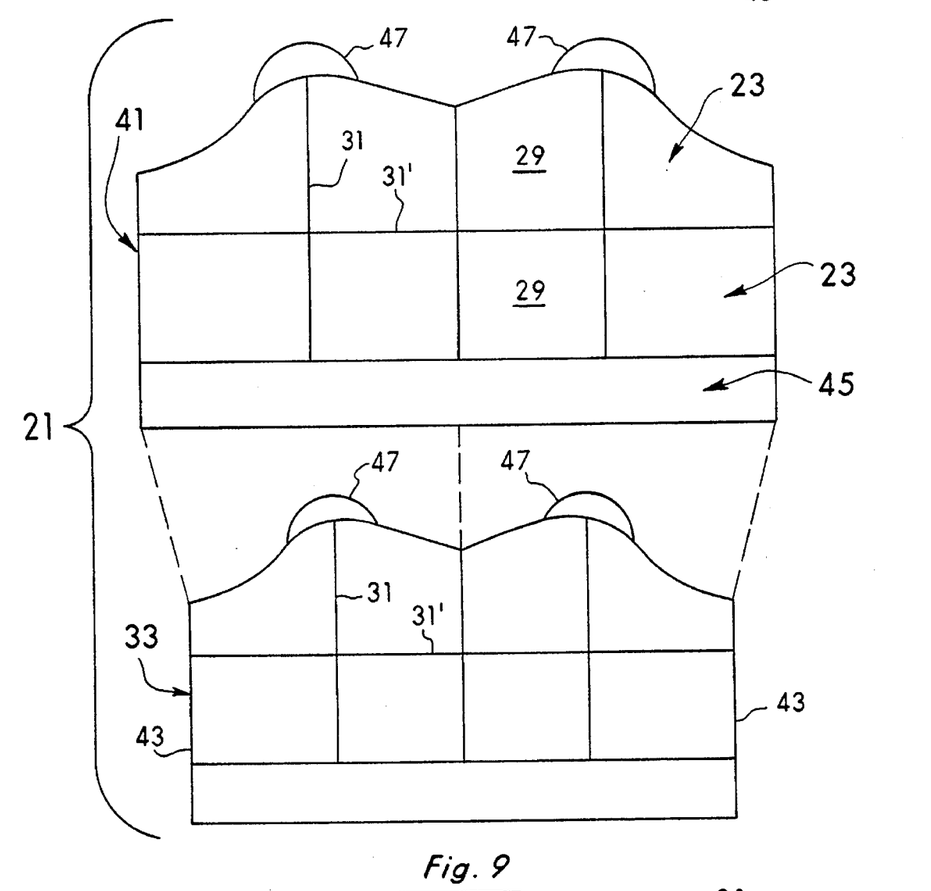
FIG. 9 is a schematic view of the relative sizing between the sheet forming the outer layer of the pouches and the smaller backing fabric of the pad member.

The pad member 21 in an unwrapped or laid open position is shown in the schematic, cross-sectional view of FIG. 8. As illustrated, the fluid pouches 23 are secured along seams 31 atop the stretchable backing fabric 33. The backing fabric 33 (e.g., Lycra) preferably has a layer of urethane 33' on its inner surface (see FIG. 5) to which the pouches 23 are actually sealed so as not to penetrate the main body of the fabric 33 itself. In one manner of manufacture to accomplish this and to create the wrinkles or folds at the boundary segments 37, the stretchable back fabric 33 can be dimensioned in all directions smaller than the sheets 41 forming the inner and outer layers 27 and 29 of the pouches 23. This is shown in FIG. 9 in which sheet 41 forming the outer pouch layers 29 (with the sheet forming inner pouch layers 27 immediately behind it) is secured to the smaller stretchable back fabric 33 along the seam lines 31 and 31'. Physically, the portions of sheet 41 to be sealed at 31 and 31' to form each pouch 23 are spaced from each other more than the corresponding portions on the undersized fabric layer 33. When sealed, this oversizing then results in the accommodating folds such as 35 and 35' in the outer layer 29 of each pouch 23 (see FIGS. 8 and 2).

Figure 10:
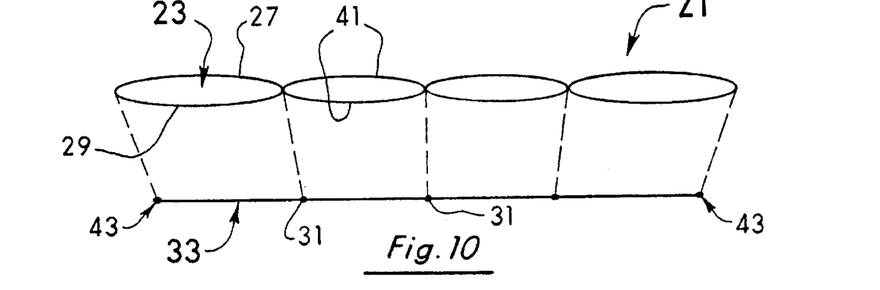
FIG. 10 is a schematic view similar to FIG. 8 illustrating how the fluid pouches are sized relative to the smaller backing fabric.

The heat sealing or joining process at 31 and 31' is preferably all done at once for ease of manufacture but it could be done, for example, in steps as illustrated in FIG. 10. In FIG. 10, the sheets 41 forming pouch layers 27 and 29 are first sealed together and then sealed to the stretchable back fabric 33. In either case, the result is the arrangement of FIG. 8 of the pad member 21 whose ends at 43 can then be secured together into a substantially cylindrical or conical shape to receive the residual limb 5. Once so fitted on the residual limb 5, the limb 5 with the sock 7 and pad member 21 about it can be inserted as a unit into the support shell 3. The stretchable, elastic nature of the fabric layer 33 helps to accommodate the fit of the pad member 21 to the residual limb 5 and helps to keep the pouches 23 firmly in place.

As best seen in FIGS. 2 and 9, the pouches 23 are preferably arranged in two, horizontal rows extending about the residual limb 5 with an elongated pouch 45 positioned below the lower row. In use when the pad member 21 is formed into a closed wrap, the elongated pouch 45 assumes a substantially annular shape and is positioned (see FIG. 2) to substantially surround the end 11 of the residual limb 5 for additional comfort and support. The tab portions 47 atop the sheet 41 and fabric 33 in FIG. 9 help the user to pull the assembled pad member 21 onto the residual limb 5.

In use, the respective seams 31 and 31' as illustrated preferably extend substantially along and about the axis 39. The division of the pad member 21 by horizontal seam 31' into at least two rows serves to aid alignment and stability of the residual limb 5 in the support shell 3. In this manner, physical displacement vertically of the fluid 25 in each pouch 23 is limited in the preferred embodiment of FIG. 2 by the horizontal seam 31'. Axial misalignment of the residual limb 5 and support shell 3 is thus also limited. Similarly, the division of each row of pouches 23 by vertical seams 31 limits horizontal or radial movement of the fluid 25 about the residual limb 5 to further limit any misalignments. This leads to improved gait and comfort, particularly over long periods of time. In operation as discussed above, the horizontally adjacent pouches 23 in each row and the vertically adjacent pouches 23 in each column move relative to each other about and along the axis 39 in essentially the same manner with essentially the same result. That is, the inner layers 27 of the horizontally and vertically adjacent pouches 23 are supported for movement including sliding movement relative to each other horizontally and vertically. In this manner, the pouches 23 can accommodate the size and shape of the residual limb 5 as well as move with it about and along the axis 39. The conforming fit and comfort of the prosthesis are thereby maximized while maintaining proper alignment for improved gait and overall operation of the prosthesis.

Figure 11:
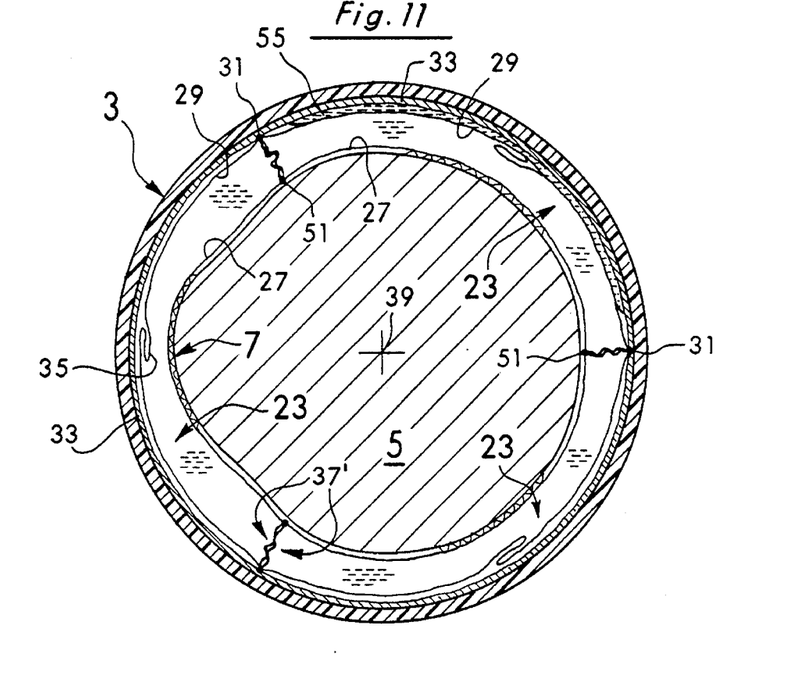
FIG. 11 is a cross-sectional view similar to FIG. 3 showing a modified embodiment of the pad member.
Figure 12:
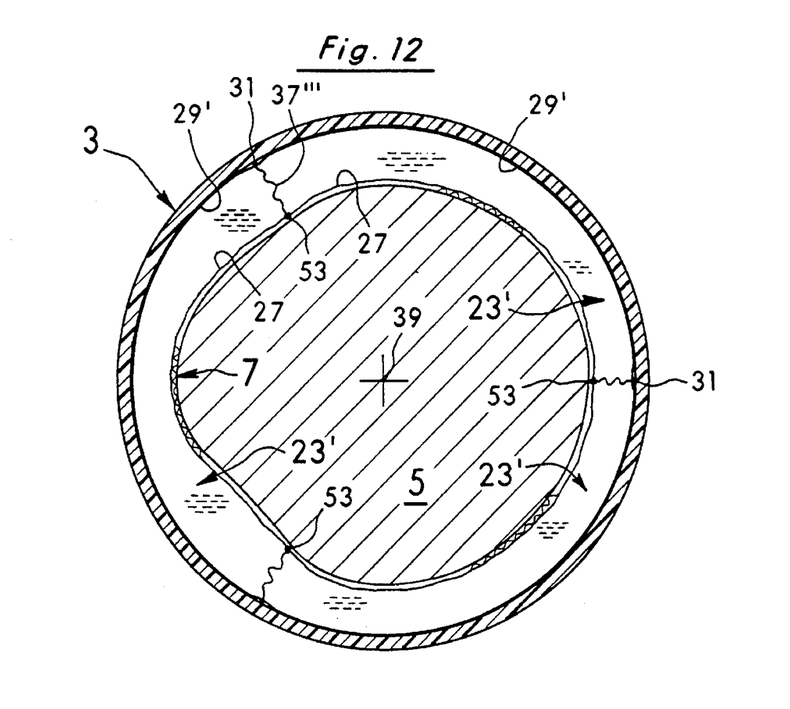
FIG. 12 is a cross-sectional view similar to FIG. 3 showing another modified embodiment of the pad member.

FIGS. 11 and 12 illustrate additional designs of the basic pad member 21. In FIG. 11, the inner pouch layers 27 are joined by additional seams 51 or other means such as patches. As shown, the additional seams 51 are located along the inner layers 27 between the seams 31 which attach the inner and outer layers 27 and 29 together. Nevertheless, the boundary segments 37' of the layers 27 are still wrinkled or folded as illustrated in FIG. 11 to provide slack in the layers 27 between the seams 31. The inner pouch layers 27 can then still move to accommodate the size and shape of the leg 5 as well as move with the leg 5 about the axis 39 without becoming tensioned or distended. The embodiment of FIG. 11 also has three pouches 23 in the modified pad member rather than the preferred four of FIGS. 1–10. However, the essential operation of pad member is still the same as the preferred pad member 21 of FIGS. 1–10.

In the embodiment of FIG. 12, the outer layer 29' of the modified pouch 23' is made to fit between seams 31 without creating the back folds 35 against the backing fabric 33 as in the preferred embodiment of FIGS. 1–10. Additionally, the outer fabric layer 33 is not used. Further, the modified pouches 23' share a common boundary segment 37'''. The inner layers 27 of adjacent pouches 23' are also secured together at locations 53 between the seams 31 which attach the inner and outer layers 27 and 29' together. Nevertheless, as in the embodiment of FIG. 11, the boundary segments 37''' are still wrinkled and folded to accommodate and move with the leg 5 without becoming tensioned or distended.

Figure 13:
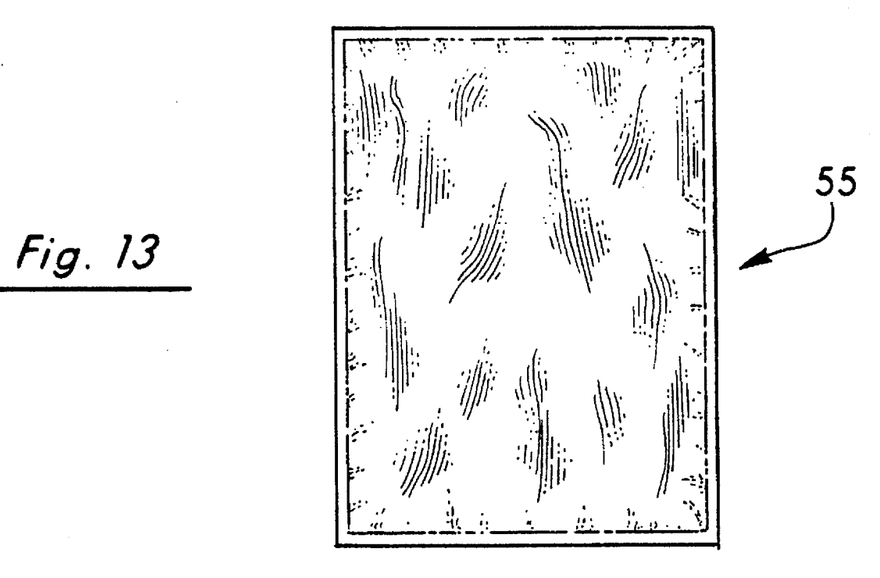
FIG. 13 illustrates a supplemental pad intended to be placed between the fluid pouches and backing fabric of the pad member to adjust the fit and comfort of the prosthesis.

The embodiment of FIG. 11 also shows the use of a small, supplemental pad 55. The pad 55 like pouch 23 is at least partially filled with fluid and can be manually placed between the outer layer 29 of the pouch 23 and the backing fabric 33. The supplemental pad 55 can be of a number of shapes, sizes, and thicknesses such as the simple rectangular one of FIG. 13. In use, the supplemental pad 55 serves to refine or fine tune the fit of the prosthesis for additional comfort and stability.

While several embodiments of the invention have been shown and described in detail, it is to be understood that various modifications and changes could be made to them without departing from the scope of the invention. For example, the present invention has been described and illustrated in use with a below the knee prosthesis but is equally adaptable for use with an above the knee prosthesis or with other body parts such as arms.

We claim:

1. A prosthetic device primarily intended for use with a residual limb, said prosthetic device including:

a relatively rigid, support shell having an inner surface extending substantially about an axis and dimensioned to receive at least a portion of said residual limb and a pad member, said pad member including at least a first pouch at least partially filled with a liquid and means for positioning said pouch of said pad member between said residual limb portion and the inner surface of said support shell, said pouch having inner and outer layers extending at least partially about and along said axis with said liquid being positioned between said inner and outer layers, said inner layer being made of flexible material and said pad member further including means for creating wrinkles in at least a portion of said inner layer, said inner layer of said pouch having at least two boundary segments extending substantially along said axis and spaced from each other about said axis, said wrinkle creating means including means for substantially preventing said inner layer from being placed under tension about said axis between said boundary segments.

2. The prosthetic device of claim 1 wherein said liquid is a highly viscous liquid.

3. A prosthetic device primarily intended for use with a residual limb, said prosthetic device including:

a relatively rigid, support shell having an inner surface extending substantially about an axis and dimensioned to receive at least a portion of said residual limb and a pad member, said pad member including at least a first pouch at least partially filled with a liquid and means for positioning said pouch of said pad member between said residual limb portion and the inner surface of said support shell, said pouch having inner and outer layers extending at least partially about and along said axis with said liquid being positioned between said inner and outer layers, said inner layer being made of flexible material and said pad member further including means for creating wrinkles in at least a portion of said inner layer, said inner layer of said pouch having at least two boundary segments extending substantially along said axis and spaced from each other about said axis, said wrinkle creating means including means for substantially preventing said inner layer from being distended about said axis between said boundary segments.

4. A prosthetic device primarily intended for use with a residual limb, said prosthetic device including:

a relatively rigid, support shell having an inner surface extending substantially about an axis and dimensioned to receive at least a portion of said residual limb and a pad member, said pad member including at least a first pouch at least partially filled with a liquid and means for positioning said pouch of said pad member between said residual limb portion and the inner surface of said support shell, said pouch having inner and outer layers extending at least partially about and along said axis with said liquid being positioned between said inner and outer layers, said inner layer being made of flexible material and said pad member further including means for creating wrinkles in at least a portion of said inner layer, said inner layer of said pouch having portions folding back on one another to create said wrinkles.

5. A prosthetic device primarily intended for use with a residual limb, said prosthetic device including:

a relatively rigid, support shell having an inner surface extending substantially about an axis and dimensioned to receive at least a portion of said residual limb and a pad member, said pad member including at least a first pouch at least partially filled with a liquid and means for positioning said pouch of said pad member between said residual limb portion and the inner surface of said support shell, said pouch having inner and outer layers extending at least partially about and along said axis with said liquid being positioned between said inner and outer layers, said inner layer being made of flexible material and said pad member further including means for creating wrinkles in at least a portion of said inner layer, said pouch having at least two boundary segments extending substantially along said axis and spaced from each other about said axis wherein said wrinkle creating means creates wrinkles in the inner layer of said pouch in at least one of said boundary segments.

6. The prosthetic device of claim 5 wherein said wrinkle creating means creates wrinkles in the inner layer of said pouch in each of said boundary segments.

7. A prosthetic device primarily intended for use with a residual limb, said prosthetic device including:

a relatively rigid, support shell having an inner surface extending substantially about an axis and dimensioned to receive at least a portion of said residual limb and a pad member, said pad member including at least a first pouch at least partially filled with a liquid and means for positioning said pouch of said pad member between said residual limb portion and the inner surface of said support shell, said pouch having inner and outer layers extending at least partially about and along said axis with said liquid being positioned between said inner and outer layers, said inner layer being made of flexible material and said pad member further including means for creating wrinkles in at least a portion of said inner layer and means for maintaining the outer layer of said pouch in a substantially fixed position relative to the inner surface of said support shell wherein said wrinkle creating means includes means for permitting said inner layer to move radially about said axis relative to said outer layer.

8. A prosthetic device primarily intended for use with a residual limb, said prosthetic device including:

a relatively rigid, support shell having an inner surface extending substantially about an axis and dimensioned to receive at least a portion of said residual limb and a pad member, said pad member including at least a first pouch at least partially filled with a liquid and means for positioning said pouch of said pad member between said residual limb portion and the inner surface of said support shell, said pouch having inner and outer layers extending at least partially about and along said axis with said liquid being positioned between said inner and outer layers, said inner layer being made of flexible material and said pad member further including means for permitting at least portions of said inner layer to be folded back on one another and means for maintaining portions of said inner layer folded back on one another to substantially prevent said inner layer from being placed under tension about said axis.

9. The prosthetic device of claim 8 wherein said liquid is a highly viscous liquid.

10. A prosthetic device primarily intended for use with a residual limb, said prosthetic device including:

a relatively rigid, support shell having an inner surface extending substantially about an axis and dimensioned to receive at least a portion of said residual limb and a pad member, said pad member including at least a first pouch at least partially filled with a liquid and means for positioning said pouch of said pad member between said residual limb portion and the inner surface of said support shell, said pouch having inner and outer layers extending at least partially about and along said axis with said liquid being positioned between said inner and outer layers, said inner layer being made of flexible material and said pad member further including means for permitting at least portions of said inner layer to be folded back on one another and means for maintaining portions of said inner layer folded back on one another to substantially prevent said inner layer from being distended about said axis.

11. A prosthetic device primarily intended for use with a residual limb, said prosthetic device including:

a relatively rigid, support shell having an inner surface extending substantially about an axis and dimensioned to receive at least a portion of said residual limb and a pad member, said pad member including at least a first pouch at least partially filled with a liquid and means for positioning said pouch of said pad member between said residual limb portion and the inner surface of said support shell, said pouch having inner and outer layers extending at least partially about and along said axis with said liquid being positioned between said inner and outer layers, said inner layer being made of flexible material and said pad member further including means for permitting at least portions of said inner layer to be folded back on one another, said means for permitting at least portions of said inner layer to be folded back on one another including a second pouch at least partially filled with a fluid and means for positioning said second pouch immediately adjacent said first pouch with at least portions of each pouch abutting one another.

12. The prosthetic device of claim 11 wherein said second pouch has inner and outer layers extending at least partially about and along said axis with said fluid being positioned between said inner and outer layers, said pad member further including means for supporting said inner layers of said pouches for movement relative to each other.

13. The prosthetic device of claim 12 wherein each inner layer of each pouch has a boundary segment extending substantially along said axis and said supporting means supports said boundary segments immediately adjacent and abutting one another, said supporting means supporting the abutting boundary segments of said pouches for sliding movement relative to each other.

14. The prosthetic device of claim 11 wherein the fluid in said second pouch is substantially incompressible and said abutting portions serve to maintain the fluid pressure in said adjacent pouches substantially the same to thereby apply substantially uniform pressure to the residual limb portion.

15. A prosthetic device primarily intended for use with a residual limb, said prosthetic device including:

a relatively rigid, support shell having an inner surface extending substantially about an axis and dimensioned to receive at least a portion of said residual limb and a pad member, said pad member including at least a first pouch at least partially filled with a fluid and means for positioning said pouch of said pad member between said residual limb portion and the inner surface of said support shell, said pouch having inner and outer layers extending at least partially about and along said axis with said fluid being positioned between said inner and outer layers, said inner layer being made of flexible material and said pad member further including means for permitting at least portions of said inner layer to be folded back on one another, said means for permitting at least portions of said inner layer to be folded back on one another including a second pouch at least partially filled with a fluid and means for positioning said second pouch immediately adjacent said first pouch with at least portions of each pouch abutting one another, said second pouch having inner and outer layers extending at least partially about and along said axis with said fluid being positioned between said inner and outer layers, said pad member further including means for supporting said inner layers of said pouches for movement relative to each other wherein each inner layer of each pouch has a boundary segment extending substantially along said axis and said supporting means supports said boundary segments immediately adjacent and abutting one another, each boundary segment of each inner layer having portions folded back on one another and folded back on the folded portions of the abutting boundary segment of the inner layer of the adjacent pouch.

16. The prosthetic device of claim 15 wherein each of said boundary segments extends away from the respective outer layer of each pouch and said pad member further includes means for securing said adjacent boundary segments to each other at a location spaced from said respective outer layers.

17. A prosthetic device primarily intended for use with a residual limb, said prosthetic device including:

a relatively rigid, support shell having an inner surface extending substantially about an axis and dimensioned to receive at least a portion of said residual limb and a pad member, said pad member including at least a first pouch at least partially filled with a liquid and means for positioning said pouch of said pad member between said residual limb portion and the inner surface of said support shell, said pouch having inner and outer layers extending at least partially about and along said axis with said liquid being positioned between said inner and outer layers, said inner layer being made of flexible material and said pad member further including means for permitting at least portions of said inner layer to be folded back on one another, said means for permitting at least portions of said inner layer to be folded back on one another including a second pouch at least partially filled with a fluid and means for positioning said second pouch immediately adjacent said first pouch, said inner layers of said adjacent pouches having a common boundary segment with portions of said common boundary segment being folded back on one another.

18. A prosthetic device primarily intended for use with a residual limb, said prosthetic device including:

a relatively rigid, support shell having an inner surface extending substantially about an axis and dimensioned to receive at least a portion of said residual limb and a pad member, said pad member including at least a first pouch at least partially filled with a liquid and means for positioning said pouch of said pad member between said residual limb portion and the inner surface of said support shell, said pouch having inner and outer layers extending at least partially about and along said axis with said liquid being positioned between said inner and outer layers, said inner layer being made of flexible material and said pad member further including means for maintaining the outer layer of said pouch in a substantially fixed position relative to the inner surface of said support shell and means for permitting at least portions of said inner layer of said pouch to move radially about said axis relative to said outer layer.

19. The prosthetic device of claim 18 wherein said inner layer of said pouch has at least two boundary segments extending substantially along said axis and spaced from each other about said axis and means for substantially preventing said inner layer from being placed under tension about said axis between said boundary segments.

20. The prosthetic device of claim 18 wherein said inner layer of said pouch has at least two boundary segments extending substantially along said axis and spaced from each other about said axis and means for substantially preventing said inner layer from being distended about said axis between said boundary segments.

21. The prosthetic device of claim 18 wherein said inner layer of said pouch has two portions folding back on one another to create slack in said inner layer to permit said radial movement of said inner layer relative to said outer layer.

22. The prosthetic device of claim 18 wherein said liquid is a highly viscous liquid.

23. The prosthetic device of claim 18 further including a backing layer, said backing layer extending at least partially about and along said axis between said outer pouch layer and said support shell.

24. The prosthetic device of claim 23 wherein said backing layer is made of stretchable material.

25. The prosthetic device of claim 23 wherein said backing layer is made of elastic material.

26. The prosthetic device of claim 23 further including a supplemental pad at least partially filled with fluid and dimensioned to be placed between said backing layer and said outer pouch layer.

27. A prosthetic device primarily intended for use with a residual limb, said prosthetic device including:

a relatively rigid, support shell having an inner surface extending substantially about an axis and dimensioned to receive at least a portion of said residual limb and a pad member, said pad member including at least a first pouch at least partially filled with a fluid and means for positioning said pouch of said pad member between said residual limb portion and the inner surface of said support shell, said pouch having inner and outer layers extending at least partially about and along said axis with said fluid being positioned between said inner and outer layers, said inner layer being made of flexible material and said pad member further including means for maintaining the outer layer of said pouch in a substantially fixed position relative to the inner surface of said support shell and means for permitting at least portions of said inner layer of said pouch to move radially about said axis relative to said outer layer, said prosthetic device further including a backing layer, said backing layer extending at least partially about and along said axis between said outer pouch layer and said support shell wherein said backing layer is dimensioned smaller about said axis between first and second portions thereof than said outer pouch layer is dimensioned about said axis between first and second portions thereof, said prosthetic device further including means for securing together said respective first and second portions of said backing layer and said outer pouch layer wherein said outer pouch layer folds over itself between the first and second portions thereof to accommodate the smaller dimensioned backing layer.

28. A prosthetic device primarily intended for use with a residual limb, said prosthetic device including:

a relatively rigid, support shell having an inner surface extending substantially about an axis and dimensioned to receive at least a portion of said residual limb and a pad member, said pad member having at least two pouches at least partially filled with a liquid and means for positioning said pouches adjacent one another between said residual limb portion and the inner surface of said support shell, each of said pouches having inner and outer layers extending at least partially about and along said axis with said liquid being positioned between said inner and outer layers, said inner layers being made of flexible material and said positioning means further including means for supporting the inner layers of said two adjacent pouches for sliding movement relative to and across each other.

29. The prosthetic device of claim 28 wherein each of the inner layers of said adjacent pouches has a boundary segment and said supporting means supports said boundary segments immediately adjacent and abutting one another for sliding movement relative to and across one another.

30. The prosthetic device of claim 28 wherein said at least two pouches are positioned radially adjacent one another about said axis and said inner layers thereof are supported for sliding movement relative to and across each other about said axis.

31. The prosthetic device of claim 28 wherein said at least two pouches are positioned axially adjacent one another along said axis and said inner layers thereof are supported for sliding movement relative to and across each other along said axis.

32. The prosthetic device of claim 28 wherein said pad member includes at least three pouches at least partially filled with liquid with each pouch having inner and outer layers extending at least partially about and along said axis with said liquid being positioned between the inner and outer layers, said positioning means positioning the first and second of said pouches adjacent each other radially about said axis and including means for supporting said first and second pouches for sliding movement relative to and across each other radially about said axis and said positioning means further positioning said third pouch adjacent said first pouch axially along said axis and including means for supporting said first and third pouches for sliding movement relative to and across each other axially along said axis.

33. The prosthetic device of claim 28 wherein said pad member includes a plurality of adjacent pouches extending about said axis to substantially encircle said residual limb portion.

34. A prosthetic device primarily intended for use with a residual limb, said prosthetic device including:

a relatively rigid, support shell having an inner surface extending substantially about an axis and dimensioned to receive at least a portion of said residual limb and a pad member, said pad member having at least two pouches at least partially filled with a fluid and means for positioning said pouches adjacent one another between said residual limb portion and the inner surface of said support shell, each of said pouches having inner and outer layers extending at least partially about and along said axis with said fluid being positioned between said inner and outer layers, said inner layers being made of flexible material and said positioning means further including means for supporting the inner layers of said two adjacent pouches for sliding movement relative to each other, each of the inner layers of said adjacent pouches having a boundary segment and said supporting means supports said boundary segments immediately adjacent and abutting one another for sliding movement relative to one another wherein each boundary segment of each inner layer has portions folded back on each other and folded back on the folded portions of the abutting boundary segment of the inner layer of the adjacent pouch.

35. A prosthetic device primarily intended for use with a residual limb, said prosthetic device including:

a relatively rigid, support shell having an inner surface extending substantially about an axis and dimensioned to receive at least a portion of said residual limb and a pad member, said pad member having a first plurality of pouches at least partially filled with fluid and means for positioning said pouches adjacent one another and extending about said axis to substantially encircle said residual limb portion between said residual limb portion and said inner surface of said support shell, said pad member further including a second plurality of pouches at least partially filled with fluid and means for positioning said second plurality of pouches adjacent one another and extending about said axis to substantially encircle said residual limb portion between said residual limb portion and the inner surface of said support shell, said second plurality of pouches being positioned immediately adjacent said first plurality of pouches along said axis.

36. The prosthetic device of claim 35 wherein at least a first pouch in the first plurality is positioned axially adjacent at least a second pouch in the second plurality and said positioning means includes means for supporting said first and second pouches for sliding movement relative to each other along said axis.

37. The prosthetic device of claim 35 wherein said first plurality of pouches includes at least three pouches.

38. The prosthetic device of claim 35 wherein said first and second plurality of pouches respectively include at least three pouches.

39. The prosthetic device of claim 35 further including an elongated, substantially annular pouch at least partially filled with fluid and means for positioning said annular pouch adjacent said second plurality of pouches, said annular pouch extending substantially about said axis.

40. The prosthetic device of claim 35 further including means for removably securing said pad member about said residual limb portion separate from said support shell, said pad member and said residual limb portion being removably receivable as a unit in said support shell.

41. The prosthetic device of claim 35 wherein said fluid is a highly viscous liquid.

* * * * *